(12) United States Patent
Dawson et al.

(10) Patent No.: US 11,813,054 B1
(45) Date of Patent: Nov. 14, 2023

(54) METHODS, SYSTEMS, AND COMPUTER READABLE MEDIA FOR CONDUCTING AN AUTOMATIC ASSESSMENT OF POSTURAL CONTROL OF A SUBJECT

(71) Applicant: Duke University, Durham, NC (US)

(72) Inventors: Geraldine Dawson, Durham, NC (US); Guillermo Sapiro, Durham, NC (US); Jordan Hashemi, Durham, NC (US)

(73) Assignee: Duke University, Durham, NC (US)

( * ) Notice: Subject to any disclaimer, the term of this patent is extended or adjusted under 35 U.S.C. 154(b) by 765 days.

(21) Appl. No.: 16/678,828

(22) Filed: Nov. 8, 2019

Related U.S. Application Data

(60) Provisional application No. 62/757,234, filed on Nov. 8, 2018.

(51) Int. Cl.
| | | |
|---|---|---|
| *G06T 7/70* | (2017.01) | |
| *A61B 5/11* | (2006.01) | |
| *G06F 3/01* | (2006.01) | |
| *G16H 50/20* | (2018.01) | |
| *G16H 50/30* | (2018.01) | |
| *G06T 7/00* | (2017.01) | |

(52) U.S. Cl.
CPC .............. *A61B 5/1116* (2013.01); *G06F 3/012* (2013.01); *G06F 3/017* (2013.01); *G06T 7/0012* (2013.01); *G06T 7/70* (2017.01); *G16H 50/20* (2018.01); *G16H 50/30* (2018.01); *G06T 2207/30201* (2013.01)

(58) Field of Classification Search
CPC .......... A61B 5/1116; G06T 7/70; G16H 50/30; G16H 50/20; G06F 3/012; G06F 3/017; G06T 7/0012; G06T 2207/30201
See application file for complete search history.

(56) References Cited

U.S. PATENT DOCUMENTS

| | | |
|---|---|---|
| 6,231,187 B1 | 5/2001 | Munoz et al. |
| 9,530,080 B2 | 12/2016 | Glazer |

(Continued)

OTHER PUBLICATIONS

Baveye et al. "LIRIS-ACCEDE: A Video Database for Affective Content Analysis," IEEE Transactions on Affective Computing, vol. 6, pp. 43-55, 2015.

Boujarwah, et al., "Understanding the challenges and opportunities for richer descriptions of stereotypical behaviors of children with ASD: a concept exploration and validation," Proceedings of the 12th International ACM SIGACCESS Conference on Computers and Accessibility (ASSETS '10), pp. 67-74, Orlando, Fla, USA (Oct. 2010).

(Continued)

*Primary Examiner* — Terrell M Robinson
(74) *Attorney, Agent, or Firm* — Jenkins, Wilson, Taylor & Hunt, P.A.

(57) ABSTRACT

The subject matter described herein includes methods, systems, and computer readable media for conducting an automatic assessment of postural control of a subject. According to one aspect, a method occurs at a computing platform including a processor and memory. The method includes displaying a stimulus to which a subject responds, capturing facial image data of the subject, analyzing the facial image data to determine a frequency of head displacement information associated with the subject, using the head displacement information to derive postural control assessment data, and determining that the postural control assessment data is indicative of a neurodevelopmental or neuropsychiatric disorder associated with the subject.

20 Claims, 5 Drawing Sheets
(3 of 5 Drawing Sheet(s) Filed in Color)

(56) References Cited

U.S. PATENT DOCUMENTS

| | | | |
|---|---|---|---|
| 9,767,349 | B1 | 9/2017 | Shreve et al. |
| 10,165,176 | B2 | 12/2018 | Frahm et al. |
| 11,158,403 | B1 | 10/2021 | Sapiro et al. |
| 11,580,874 | B1 | 2/2023 | Sapiro et al. |
| 2004/0210159 | A1 | 10/2004 | Kibar |
| 2008/0068186 | A1 | 3/2008 | Bonefas et al. |
| 2008/0227063 | A1 | 9/2008 | Kenedy et al. |
| 2009/0271740 | A1* | 10/2009 | Ryan-Hutton et al. . G06Q 30/00 715/835 |
| 2009/0285456 | A1* | 11/2009 | Moon et al. ......... G06V 40/176 382/118 |
| 2011/0152711 | A1* | 6/2011 | Della Santina et al. ..................... A61B 3/0083 600/595 |
| 2012/0002848 | A1* | 1/2012 | Hill .................. G16Z 99/00 382/118 |
| 2012/0293773 | A1 | 11/2012 | Publicover et al. |
| 2012/0310117 | A1* | 12/2012 | Teicher et al. ......... A61B 5/168 600/595 |
| 2012/0314045 | A1 | 12/2012 | Billard et al. |
| 2014/0087340 | A1* | 3/2014 | Maher ................. G09B 19/00 434/247 |
| 2014/0153794 | A1 | 6/2014 | Varaklis et al. |
| 2014/0315168 | A1 | 10/2014 | Movellan et al. |
| 2015/0099946 | A1 | 4/2015 | Sahin |
| 2015/0282705 | A1 | 10/2015 | Avital |
| 2015/0288877 | A1 | 10/2015 | Glazer |
| 2016/0128617 | A1 | 5/2016 | Morris et al. |
| 2016/0309081 | A1 | 10/2016 | Frahm et al. |
| 2017/0046567 | A1 | 2/2017 | Hong et al. |
| 2017/0184846 | A1 | 6/2017 | Lu |
| 2017/0206412 | A1 | 7/2017 | Kaehler |
| 2017/0365101 | A1 | 12/2017 | Samec et al. |
| 2018/0098724 | A1 | 4/2018 | Lu et al. |
| 2019/0029585 | A1 | 1/2019 | Geva et al. |
| 2019/0089946 | A1 | 3/2019 | Watari et al. |
| 2019/0125180 | A1 | 5/2019 | Arnold et al. |
| 2019/0139438 | A1 | 5/2019 | Tu et al. |

OTHER PUBLICATIONS

Elsabbagh, et al., "Visual orienting in the early broader autism phenotype: disengagement and facilitation," Journal of Child Psychology and Psychiatry and Allied Disciplines, vol. 50, No. 5, pp. 637-642 (2009).

Howard, et al., "A comparison of intensive behavior analytic and eclectic treatments for young children with autism," Research in Developmental Disabilities, vol. 26, No. 4, pp. 359-383 2005.

Interview Summary corresponding to U.S. Appl. No. 15/141,391 dated Sep. 25, 2019.

Jones et al. "Reduced engagement with social stimuli in 6-month-old infants with later autism spectrum disorder: A longitudinal prospective study of infants at high familial risk," Journal of Neurodevelopmental Disorders, 8:7, pp.1-20 (2016).

Marko et al. "Behavioural and neural basis of anomalous motor learning in children with autism," Brain, 138 (Pt 3): pp. 784-797 (2015).

Nichols, et al, "Social Smiling and its Components in High-risk Infant Siblings Without Later ASD Symptomatology," J Autism Dev Disord, vol. 44, No. 4, pp. 894-902 (2014).

Rudovic, et al, "Coupled Gaussian processes for pose-invariant facial expression recognition," PAMI, vol. 35, No. 6, pp. 1357-1369 (2013).

Zappella et al. "What do home videos tell us about early motor and socio-communicative behaviours in children with autistic features during the second year of life--An exploratory study," Author Manuscript, pp. 1-18 [Published in final edited form as: Early Hum Dev, 91(10), pp. 569-575 (2015)].

Reiersen et al. "Co-occurrence of Motor Problems and Autistic Symptoms in Attention-Deficit/Hyperactivity Disorder," J Am Acad Child Adolesc Psychiatry, 47(6), pp. 662-672 (2008). Hyperactivity Disorder," J Am Acad Child Adolesc Psychiatry,47(6), pp.662-672 (2008).

Baranek, G.T., "Autism during infancy: a retrospective video analysis of sensory-motor and social behaviors at 9-12 months of age," Journal of Autism and Developmental Disorders, vol. 29, No. 3, pp. 213-224 (1999).

"Computer vision of facial dynamics in infants at risk for autism," Job offer listed on Euraxess, pp. 1-4 (2017) [Accessed online Aug. 14, 2020].

Adrien et al., "Autism and family home movies: preliminary findings," Journal of Autism and Developmental Disorders, vol. 21(1), pp. 43-49, (1991).

Adrien et al., "Early symptoms in autism from family home movies. Evaluation and comparison between 1st and 2nd year of life using I.B.S.E. scale," Acta Paedopsychiatrica, vol. 55, No. 2, pp. 71-75, (1992).

Aharon, et al., "K-SVD: An Algorithm for Designing Overcomplete Dictionaries for Sparse Representation," IEEE Trans Signal Process, vol. 54, No. 11, pp. 4311-4322 (2006).

Anzulewicz et al. "Toward the Autism Motor Signature: Gesture patterns during smart tablet gameplay identify children with autism," Sci Rep, Vol. 6, pp. 31107-1 - 31107-13 (2016).

Arvin, M., "Navy Funds Autism-Screening App, Hoping for Help with PTSD", Artificial Intelligence Online, pp. 1-6 (Mar. 20, 2016).

Baltrusaitis et al. "Openface 2.0: Facial Behavior Analysis Toolkit," IEEE International Conference on Automatic Face and Gesture Recognition (2018).

Baltrusaitis et al. "Openface: An open source facial behavior analysis toolkit," IEEE Winter Conference on Applications of Computer Vision (WACV), p. 1-10 (2016).

Bloch et al., "On the onset of eye-head coordination in infants," Behavioural Brain Research, vol. 49, No. 1, pp. 85-90 (1992).

Brisson et al. "Motor anticipation failure in infants with autism: a retrospective analysis of feeding situations," Autism, 16(4), pp. 420-429 (2012).

Bryson et al, "A prospective case series of high-risk infants who developed autism," (SpringerLink) Journal of Autism and Developmental Disorders, vol. 37, No. 1, pp. 12-24 (2007).

Bryson, et al., "The autism observation scale for infants: scale development and reliability data," (SpringerLink) Journal of Autism and Developmental Disorders, vol. 38, No. 4, pp. 731-738 (25 pages) (2008).

Campbell et al. "Computer Vision Analysis Captures Atypical Attention in Toddlers with Autism," Author manuscript, . 1-19 [Published in final edited form as: Autism, 23(3), pp. 619-628 (2019)].

Campbell et al. "Computer vision analysis captures atypical attention in toddlers with autism," Autism, Vol. 23(3), pp. 619-628 (2018).

Campbell et al. "Use of a Digital Modified Checklist for Autism in Toddlers - Revised with Follow-up to Improve Quality of Screening for Autism," The Journal of Pediatrics, Vol. 183, pp. 133-139 (2017).

Chang et al. "Synthesis-based Low-cost Gaze Analysis," International Conference on Human-Computer Interaction, pp. 1-6, Jul. 2016.

Chang, et al, "LIBSVM: a library for support vector machines," ACM Trans Intelligent Systems and Technology, vol. 2, No. 3, pp. 1-39 (2011).

Chawarska et al. "Decreased Spontaneous Attention to Social Scenes in 6-Month-Old Infants Later Diagnosed with Autism Spectrum Disorders," Biological Psychiatry, No. 74(3), pp. 195-203 (2013).

Commonly-assigned, Co-pending U.S. Appl. No. 15/141,391 for "Methods, Systems, and Computer Readable Media for Automated Behavioral Assessment," (Unpublished, filed Apr. 28, 2016).

Commonly-assigned, Co-pending U.S. Appl. No. 16/678,789 for "Methods, Systems, and Computer Readable Media for Automated Attention Assessment," (Unpublished, filed Nov. 8, 2019).

Constantino et al. "Infant viewing of social scenes is under genetic control and is atypical in autism," Author manuscript, pp. 1-41 [Published in final edited form as: Nature, Vol. 547(7663), pp. 340-344, (2017)].

(56) References Cited

OTHER PUBLICATIONS

Cook et al. "Atypical basic movement kinematics in autism spectrum conditions," Brain, 136 (Pt 9), pp. 2816-2824 (2013).
Dalal, et al, "Histograms of oriented gradients for human detection," Proceedings of the IEEE Computer Society Conference on Computer Vision and Pattern Recognition (CVPR '05), pp. 886-893, San Diego, USA, pp. 1-9 (Jun. 2005).
Dawson et al. "Case Study of the Development of an Infant with Autism from Birth to Two Years of Age," Author manuscript, pp. 1-14 [Published in final edited form as: J Appl Dev Psychol, 21(3), pp. 299-313 (2000)].
Dawson et al. "Children with Autism Fail to Orient to Naturally Occurring Social Stimuli," Journal of Autism and Developmental Disorders, Vol. 28, No. 6, pp. 479-485 (1998).
Dawson, G., "Early behavioral intervention, brain plasticity, and the prevention of autism spectrum disorder," Development and Psychopathology, vol. 20, No. 3, pp. 775-803 (2008).
Dawson, K. Toth, R. Abbott, et al., "Early Social Attention Impairments in Autism: Social Orienting, Joint Attention, and Attention to Distress," Developmental Psychology, No. 40(2), pp. 271-283 (2004).
De la Torre et al., "IntraFace," Author manuscript, pp. 1-30 [published in final edited form as: IEEE Int Conf Autom Face Gesture Recognit Workshops] (2015).
Dementhon et al. "Model-Based Object Pose in 25 Lines of Code," International Journal of Computer Vision, 15(1), pp. 123-141 (1995).
Downing, et al., "Can the AOSI at nine months discriminate between infants at high or low risk for ASD?", International Meeting for Autism Research (IMFAR '11), San Diego, Calif, USA (2011).
Egger, et al. "Automatic emotion and attention analysis of young children at home: A Research Kit autism feasibility study," npj Nature Digital Medicine, 20, pp.1-10 (2018).
Elsabbagh, et al., "Disengagement of Visual Attention in Infancy is Associated with Emerging Autism in Toddlerhood," Biological Psychiatry, vol. 74, No. 3, pp. 189-194 (2013).
Esler et al. "The Autism Diagnostic Observation Schedule, Toddler Module: Standardized Severity Scores," Author manuscript, pp. 1-28, [Published in final edited form as J Autism Dev Disord, Vol. 45 (9), pp. 2704-2720 (2015)].
Esposito et al. "An exploration of symmetry in early autism spectrum disorders: Analysis of lying," Brain Dev, 31(2), pp. 131-138 (2009).
Esposito, et al., "Analysis of unsupported gait in toddlers with autism," Brain and Development, vol. 33, No. 5, pp. 367-373 (2011).
Everingham, et al., ""Hello! My name is... Buffy"--automatic naming of characters in TV video," Proceedings of the British Machine Vision Conference (BMVC '06), Edinburgh, UK (2006).
Fischler et al. "Random Sample Consensus: A Paradigm for Model Fitting with Applications to Image Analysis and Automated Cartography," Commun. ACM, Vol. 24, No. 6, pp. 381-395 (1981).
Flanagan et al. "Head Lag in Infants at Risk for Autism: A Preliminary Study," Am J Occup Ther, 66 (5), pp. 577-585 (2012).
Freeth, et al., "The Influence of visual salienxcy on fixation patterns in individuals with autism spectrum disorders," Neuropsychologia, vol. 49, No. 1, pp. 156-160 (2011).
Ghanouni et al. "Effect of Social Stimuli on Postural Responses in Individuals with Autism Spectrum Disorder," J Autism Dev Disord, 47(5), pp. 1305-1313 (2017).
Gima et al. "Early motor signs of autism spectrum disorder in spontaneous position and movement of the head," Exp Brain Res, 236(4), pp. 1139-1148 (2018).
Goodwin, et al., "Automated detection of stereotypical motor movements," Journal of Autism and Developmental Disorders, vol. 41, no. 6, pp. 770-782 (2011).
Gotham et al. "The Autism Diagnostic Observation Schedule: Revised Algorithms for Improved Diagnostic Validity," Journal of Autism and Developmental Disorders, 37(4), pp. 613-627 (2007).
Gouleme et al. "Postural Control and Emotion in Children with Autism Spectrum Disorders," Transl Neurosci, 8, pp. 158-166 (2017).
Gross, et al, "Multi-PIE," FG, 2010, pp. 807-813.
Guney, et al."Cross-pose facial expression recognition," FG, pp. 1-6 (2013).
Hashemi et al. "A scalable app for measuring autism risk behaviors in young children: A technical validity and feasibility study," MobiHealth, pp. 1-5 (2015).
Hashemi et al. "Computer Vision Analysis for Quantification of Autism Risk Behaviors," IEEE Transactions on Affective Computing, pp. 1-12 (2018).
Hashemi, et al, "Computer vision tools for low-cost and non-invasive measurement of autism-related behaviors in infants," Autism Research and Treatment, 935686 (2014).
Hashemi, et al., "A computer vision approach for the assessment of autism-related behavioral markers," IEEE International Conference on Development and Learning and Epigenetic Robotics (ICDL), San Diego, CA, 2012, pp. 1-7 (2012).
Hastie, et al, "The Elements of Statistical Learning", Springer-Verlag (2009).
Heiser et al. "Objective measurement of hyperactivity, impulsivity, and inattention in children with hyperkinetic disorders before and after treatment with methylphenidate," Eur Child Adolesc Psychiatry, 13(2), pp. 100-104 (2004).
Hytönen et al. "Postural Control and Age," Acta Otolaryngol, 113(2), pp. 119-122 (1993).
Interview Summary corresponding to U.S. Appl. No. 15/141,391 dated Feb. 12, 2020.
Interview Summary corresponding to U.S. Appl. No. 15/141,391 dated Feb. 16, 2021.
Jeni et al. "Dense 3D Face Alignment from 2D Videos in Real-Time," 2015 11th IEEE International Conference and Workshops on Automatic Face and Gesture Recognition (FG), pp. 1-8, May 4-8, 2015, DOI: 10.1109/FG.2015.7163142, Date Added to IEEE Xplore: Jul. 23, 2015.
Jeni et al. "Person-Independent 3D Gaze Estimation Using Face Frontalization," 2016 IEEE Conference on Computer Vision and Pattern Recognition Workshops (CVPRW) DOI: 10.1109/CVPRW.2016.104.
Jones et al., "Attention to Eyes is Present But in Decline in 2-6 Month-Olds Later Diagnosed with Autism," Nature, Vol. 504, pp. 427-431 (2013).
Jones, et al., "Absence of Preferential Looking to the Eyes of Approaching Adults Predicts Level of Social Disability in 2-Year-Old Toddlers with Autism Spectrum Disorder," Archives of General Psychiatry, vol. 65, No. 8, 946-954 (2008).
Kalal, et al., "Face-TLD: Tracking-Learning-Detection Applied to Faces," Proceedings of 2010 IEEE 17th International Conference on Image Processing (ICIP '10), Hong Kong, pp. 3789-3792 (Sep. 2010).
Kang et al. "Automated Tracking and Quantification of Autistic Behavioral Symptoms Using Microsoft Kinect," Stud Health Technol Inform, 220, pp. 167-170 (2016).
Kirchner et al. "Autistic Symptomatology, Face Processing Abilities, and Eye Fixation Patterns," Journal of Autism and Developmental Disorders, 41(2), pp. 158-167 (2011).
Klin et al. "Social visual engagement in infants and toddlers with autism: Early developmental transitions and a model of pathogenesis," Author manuscript, pp. 1-34 [Published in final edited form as: Neurosci Biobehav Rev., No. 50, pp. 189-203 (2014)].
Klin, et al., "Visual Fixation Patterns During Viewing of Naturalistic Social Situations as Predictors of Social Competence in Individuals with Autism," Archives of General Psychiatry, vol. 59, No. 9, pp. 809-816 (Sep. 2002).
Kumano, et al, "Pose-invariant facial expression recognition using variable intensity templates," IJVC, vol. 83, No. 2, pp. 178-194 (2009).
Landry, et al., "Impaired disengagement of attention in young children with autism," Journal of Child Psychology and Psychiatry and Allied Disciplines, vol. 45, No. 6, pp. 1115-1122 (2004).

(56) References Cited

OTHER PUBLICATIONS

Li, et al, "Learning to predict gaze in egocentric video," Proceedings of the International Conference on Computer Vision (ICCV'13), Sydney, Australia (2013).
Lim et al. "Effect of Visual Information on Postural Control in Adults with Autism Spectrum Disorder," J Autism Dev Disord, 49, pp. 4731-4739 (2019).
Losche, et al, "Sensorimotor and action development in autistic children from infancy to early childhood," Journal of Child Psychology and Psychiatry and Allied Disciplines, vol. 31, No. 5, pp. 749-761 (1990).
Lucas da Silva et al. "A Web-Based Application to Address Individual Interests of Children with Autism Spectrum Disorders," Procedia Computer Science, vol. 14, pp. 20-27, (2012).
Lucas da Silva et al. "Inducing behavior change in children with Autism Spectrum Disorders by monitoring their attention," Proceedings of the International Conference on Physiological Computing Systems, vol. 1, pp. 131-136 (2014).
Mannan, et al, "Automatic control of saccadic eye movements made in visual inspection of briefly presented 2-D images," Spatial vision, vol. 9, No. 3, pp. 363-386 (1995).
Martin et al. "Objective measurement of head movement differences in children with and without autism spectrum disorder," Mol Autism, 9:14, pp. 1-10 (2018).
Merin et al. "Visual Fixation Patterns during Reciprocal Social Interaction Distinguish a Subgroup of 6-Month-Old Infants At-Risk for Autism from Comparison Infants," J Autism Dev Disord, 37, pp. 108-121 (2007).
Metallinou et al. "Quantifying Atypicality in Affective Facial Expressions of Children with Autism Spectrum Disorders," Author Manuscript, pp. 1-12 [Published in final edited form as Proc (IEEE Int Conf Multimed Expo), 1-6 (2013)].
Minshew et al. "Underdevelopment of the postural control system in autism," Neurology, 63(11), pp. 2056-2061 (2004).
Moore, et al., "Local binary patterns for Multiview facial expression recognition," Computer Vision and Image Understanding, vol. 115, pp. 541-558 (2011).
Morris et al. "Differences in the use of vision and proprioception for postural control in autism spectrum disorder," Neuroscience, 307, pp. 273-280 (2015).
Muratori, et al, "Early signs of autism in the first year of life," in Signs of Autism in Infants: Recognition and Treatment, pp. 46-62, Karnac, London, UK (2007).
Murias et al. "Electrophysiological Biomarkers Predict Clinical Improvement in an Open-Label Trial Assessing Efficacy of Autologous Umbilical Cord Blood for Treatment of Autism," Stem Cells Translational Medicine, 7, pp. 783-791 (2018).
Murias et al. "Validation of Eye-Tracking Measures of Social Attention as a Potential Biomarker for Autism Clinical Trials," Autism Res., No. 11 (1), pp. 166-174 (2018a).
Murphy-Chutorian, et al, "Head pose estimation in computer vision: a survey," PAMI, vol. 31, No. 4, pp. 607-626 (2009).
Nadig, et al., "A prospective study of response to name in infants at risk for autism," Archives of Pediatrics and Adolescent Medicine, vol. 161, No. 4, pp. 378-383 (2007).
Norbury et al. "Eye-movement patterns are associated with communicative competence in autistic spectrum disorders," Journal of Child Psychology and Psychiatry, 50(7), pp. 834-842 (2009).
Notice of Allowance and Interview Summary corresponding to U.S. Appl. No. 15/141,391 dated Jun. 28, 2021.
Notice of Allowance corresponding to U.S. Appl. No. 16/678,789 dated Oct. 4, 2022.
Office Action corresponding to U.S. Appl. No. 15/141,391 dated Dec. 1, 2020.
Office Action corresponding to U.S. Appl. No. 15/141,391 dated Nov. 14, 2019.
Office Action corresponding to U.S. Appl. No. 15/141,391 dated Jun. 26, 2019.
Office Action corresponding to U.S. Appl. No. 15/141,391 dated May 18, 2020.
Office Action corresponding to U.S. Appl. No. 16/678,789 dated May 27, 2022.
Osterling, et al, "Early recognition of children with autism: a study of first birthday home videotapes," Journal of Autism and Developmental Disorders, vol. 24, No. 3, pp. 247-257 (1994).
Owada et al. "Computer-analyzed facial expression as a surrogate marker for autism spectrum social core symptoms," Plos One, 13(1), pp. 1-16 (2018).
Ozonoff, et al, "A Prospective Study of the Emergence of Early Behavioral Signs of Autism", J Am Acad Child Adolesc Psychiatry, vol. 49, No. 3, pp. 256-266 (Mar. 2010).
Pelphrey et al. "Visual Scanning of Faces in Autism," Journal of Autism and Developmental Disorders, Vol. 32, No. 4, pp. 249-261 (2002).
Pierce et al. "Preference for Geometric Patterns Early in Life as a Risk Factor for Autism," Author manuscript, pp. 1-20 [Published in final edited form as: Archives of General Psychiatry, No. 68(1), pp. 101-109 (2011)].
Qiu et al. "Low-cost Gaze and Pulse Analysis using RealSense," MobiHealth, pp. 1-4 (2015).
Qiu, et al, "Domain adaptive dictionary learning," in ECCV, pp. 631-645 (2012).
Rehg, et al, "Decoding children's social behavior," CVPR, pp. 3414-3421 (2013).
Rice et al. "Parsing Heterogeneity in Autism Spectrum Disorders: Visual Scanning of Dynamic Social Scenes in School-Aged Children," Author manuscript, pp. 1-17 [Published in final edited form as J Am Acad Child Adolesc Psychiatry, 51(31), pp. 238-248 (2012)].
Robins et al. "Validation of the Modified Checklist for Autism in Toddlers, Revised with Follow-up (M-CHAT-R/F)," Pediatrics, No. 133(1), pp. 37-45 (2014).
Robins et al., "Modified Checklist for Autism in Toddlers, Revised with Follow-Up (M-Chat-R/F)TM," www.mchatscreen.com, pp. 1-3 (2009).
Rodier, et al, "Converging evidence for brain stem injury in autism," Development and Psychopathology, vol. 14, No. 3, pp. 537-557 (2002).
Rudovic et al., "Personalized machine learning for robot perception of affect and engagement in autism therapy," Science Robotics, vol. 3:19, pp. 1-11 (2018).
Sandbach, et al, "Static and dynamic 3D facial expression recognition: A comprehensive survey," Image and Vision Computing, vol. 30, No. 10, pp. 683-697 (2012).
Scott, E., "App aims for faster autism diagnosis," The Arizona Republic, pp. 1-3 (Apr. 13, 2013).
Shan, et al, "Facial expression recognition based on local binary patterns: a comprehensive study," Image and Vision Computing, vol. 27, pp. 803-816 (2009).
Shattuck, et al, "Timing of identification among children with an autism spectrum disorder: findings from a population-based surveillance study," Journal of the American Academy of Child and Adolescent Psychiatry, vol. 48, No. 5, pp. 474-483 (2009).
Shi et al. "Different Visual Preference Patterns in Response to Simple and Complex Dynamic Social Stimuli in Preschool-Aged Children with Autism Spectrum Disorders," PLOS One No. 10(3), pp. 1-16 (2015).
Shic et al., "Limited Activity Monitoring in Toddlers with Autism Spectrum Disorder," Author manuscript, pp. 1-19 [Published in final edited form as: Brain Research, No. 1380, pp. 246-254 (2011)].
Silva et al. "Automated Evaluation System for Human Pupillary Behavior," Stud Health Technol Inform. 245, pp. 589-593 (2017).
Steakley, "Using Kinect cameras to automate autism diagnosis," Scope, scopeblog.stanford.edu, pp. 1-4 (2012) [Accessed online Aug. 14, 2020].
Swettenham et al. "The Frequency and Distribution of Spontaneous Attention Shifts between Social and Nonsocial Stimuli in Autistic, Typically Developing, and Nonautistic Developmentally Delayed Infants," Journal of Child Psychology and Psychiatry, Vol. 39, No. 5, pp. 747-753 (1998).

(56) References Cited

OTHER PUBLICATIONS

Taheri, et al, "Structure-preserving sparse decomposition for facial expression analysis," IEEE Trans Image Process, vol. 23, No. 8, pp. 1-12 (2013).

Tang, et al, "Non-frontal view facial expression recognition based on ergodic hidden markov model supervectors," in ICME, pp. 1202-1207 (2010).

Tassi, "Microsoft's Kinect Being Employed to Help Detect Autism Early," Forbes.com, pp. 1-3 (2012) [Accessed online Aug. 14, 2020].

Teitelbaum et al. "Movement analysis in infancy may be useful for early diagnosis of autism," Proc Natl Acad Sci USA, Vol. 95(23), pp. 13982-13987 (1998).

Tepper, et al, "Decoupled coarse-to-fine matching and nonlinear regularization for efficient motion estimation," in Proceedings of the 19th IEEE International Conference on Image Processing (ICIP '12), pp. 1517-1520, Orlando, Fla, USA (Oct. 2012).

Vatahska, et al, "Feature-based head pose estimation from images," in Proceedings of the 7th IEEE-RAS International Conference on Humanoid Robots (Humanoids '07), pp. 330-335, Pittsburgh, PA, USA (Dec. 2007).

Wang et al., "Quantifying Facial Expression Abnormality in Schizophrenia by Combining 2D and 3D Features," IEEE, pp. 1-8 (2007).

Werner et al. "Brief Report: Recognition of Autism Spectrum Disorder Before One Year of Age: A Retrospective Study Based on Home Videotapes," Journal of Autism and Developmental Disorders, Vol. 30, No. 2, pp. 157-162 (2000).

Wright, et al, "Robust face recognition via sparse representation," IEEE Transactions on Pattern Analysis (PAMI), vol. 31, No. 2, pp. 1-18 (2009).

Wu et al. "A Biomarker Characterizing Neurodevelopment with applications in Autism," Scientific reports, 8:614, pp. 1-14 (2018).

Xiong, et al, "Supervised descent method and its applications to face alignment," CVPR, pp. 532-539, (2013).

Yandell, K., "Computer vision may aid in screening for autism," SFARI Simons Foundation Autism Research Initiative, p. 1 (Jul. 16, 2014).

Ye, Z., et al., "Detecting eye contact using wearable eye-tracking glasses," in Proceedings of the 14th International Conference on Ubiquitous Computing (UbiComp '12), pp. 699-704, Pittsburgh, Pa, USA (Sep. 2012).

Yin, et al, "A 3D facial expression database for facial behavior research," in FG, pp. 211-216 (2006).

Zeng, et al, "A Survey of Affect Recognition Methods: Audio, Visual, and Spontaneous Expressions," IEEE Transactions on Pattern Analysis and Machine Intelligence (PAMI), vol. 31, No. 1, pp. 39-58 (Jan. 2009).

Zhao, et al, "A unified probabilistic framework for automatic 3D facial expression analysis based on a bayesian belief inference and statistical feature models," Image and Vision Computing, vol. 31, No. 3, pp. 231-245 (2013).

Zhu, Z., et al, "Robust real-time face pose and facial expression recovery," CVPR, pp. 681-688, (2006).

Zwaigenbaum, et al, "Behavioral manifestations of autism in the first year of life," International Journal of Developmental Neuroscience, vol. 23, No. 2-3, pp. 143-152 (2005).

\* cited by examiner

METHODS, SYSTEMS, AND COMPUTER READABLE MEDIA FOR CONDUCTING AN AUTOMATIC ASSESSMENT OF POSTURAL CONTROL OF A SUBJECT

CROSS REFERENCE TO RELATED APPLICATIONS

This application claims the benefit of U.S. Provisional Pat. Application Serial No. 62/757,234, filed Nov. 8, 2018, the disclosure of which is incorporated herein by reference in its entirety.

GOVERNMENT INTEREST

This invention was made with government support under Federal Grant No. 1P50HD093074 awarded by the National Institute for Child Health and Human Development/National institutes of Health (NICHD) and Grant No. W911NF-16-1-0088 awarded by the Army Research Office (ARMY/ARO) and Grant No. HM04761610001 awarded by the National Geospatial Intelligence Agency (NGA) and Grant No. 1712867 awarded by the National Science Foundation (NSF) and Grant No. N00014-12-1-0839 awarded by the Office of Naval Research (ONR). The government has certain rights in the invention.

TECHNICAL FIELD

The subject matter described herein relates generally to postural control assessments. More particularly, the subject matter described herein includes methods, systems, and computer readable media for conducting an automatic assessment of postural control of a subject.

BACKGROUND

Brain disorders, such neurodevelopmental disorders and neuropsychiatric disorders, affect many people throughout the world. Current estimates indicate that 1 in 9 children may have or develop a neurodevelopmental and/or neuropsychiatric disorder, such as an autism spectrum disorder (ASD), an anxiety disorder, or attention deficient and hyperactivity disorder (ADHD). For example, ASD is associated with deficits in the processing of social information and difficulties in social interaction, and individuals with ASD exhibit atypical motor ability. Such deficits in motor function are among the earliest symptoms of neuropsychiatric conditions and persist throughout life, and thus can assist in risk detection, diagnosis, and symptom monitoring throughout the lifespan. Specifically, there is evidence that suggests that notable differences in motor function can be an early indicator of ASD and other developmental disorders. One aspect of motor ability that develops during childhood is postural control, which is reflected in the ability to maintain a steady head and body position without excessive sway. Observational studies have documented differences in postural control exhibited by older children with ASD. However, these observational studies of posture control are not always quantifiable or conducted in a reliable manner.

Accordingly, a need exists for methods, systems, and computer readable media for conducting an automatic assessment of postural control of a subject.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary.

The subject matter described herein includes methods, systems, and computer readable media for conducting an automatic assessment of postural control of a subject. According to one aspect, a method for conducting an automatic assessment of postural control of a subject is provided. In some embodiments, the method occurs at a computing platform including a processor and memory. In some embodiments, the method a method occurs at a computing platform including a processor and memory. The method includes displaying a stimulus to which a subject responds, capturing facial image data of the subject, analyzing the facial image data to determine a frequency of head displacement information associated with the subject, using the head displacement information to derive postural control assessment data, and determining that the postural control assessment data is indicative of a neurodevelopmental or neuropsychiatric disorder associated with the subject.

A system for conducting an automatic assessment of postural control of a subject is also disclosed. In some embodiments, the system includes a computing platform including at least one processor and memory, wherein the computing platform is configured to display a stimulus to which a subject responds, capture facial image data of the subject, analyze the facial image data to determine a frequency of head displacement information associated with the subject, use the head displacement information to derive postural control assessment data, and determine that the postural control assessment data is indicative of a neurodevelopmental or neuropsychiatric disorder associated with the subject.

The subject matter described herein may be implemented in software in combination with hardware and/or firmware. For example, the subject matter described herein may be implemented in software executed by a processor (e.g., a hardware-based processor). In one exemplary implementation, the subject matter described herein may be implemented using a non-transitory computer readable medium having stored thereon computer executable instructions that when executed by the processor of a computer control the computer to perform steps. Exemplary computer readable media suitable for implementing the subject matter described herein include non-transitory devices, such as disk memory devices, chip memory devices, programmable logic devices, such as field programmable gate arrays, and application specific integrated circuits. In addition, a computer readable medium that implements the subject matter described herein may be located on a single device or computing platform or may be distributed across multiple devices or computing platforms.

As used herein, the term "node" refers to a physical computing platform including one or more processors and memory.

As used herein, the terms "function", "module", or "engine" refer to software in combination with hardware and/or firmware for implementing features described herein. In some embodiments, an engine may include a field-programmable gateway array (FPGA), an application-specific integrated circuit (ASIC), or a processor.

BRIEF DESCRIPTION OF THE DRAWINGS

The patent or application file contains at least one drawing executed in color. Copies of this patent or patent application publication with color drawings will be provided by the United States Patent and Trademark Office upon request and payment of the necessary fee.

The subject matter described herein will now be explained with reference to the accompanying drawings of which.

DETAILED DESCRIPTION

Figure 1:
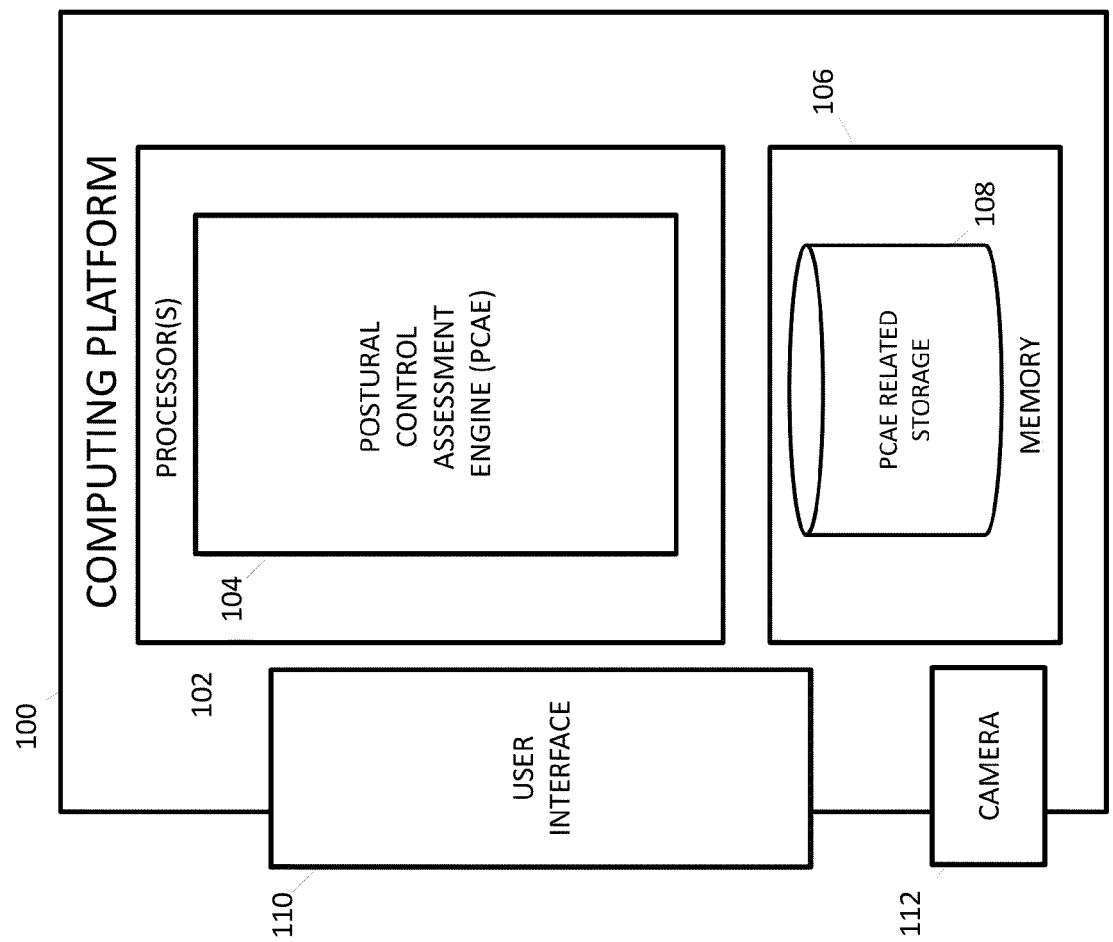
FIG. 1 is a diagram illustrating an exemplary computing platform for conducting an automatic assessment of postural control of a subject according to an embodiment of the subject matter described herein.

The subject matter described herein discloses methods, systems, and computer readable media for conducting an automatic assessment of postural control of a subject for conducting an automatic assessment of postural control of a subject. As used herein, postural control assessment refers to analyzing posture related information, e.g., detecting and monitoring a subject's head movement and/or providing an assessment based at least in part on the posture related information. Aspects of the present subject matter described herein pertain to performing automated postural control assessment. In some embodiments, an automated postural control assessment may include posture and head movement and/or displacement analysis and may occur at or be performed by an posture control assessment engine (PCAE) or application (also referred to herein as "app") executing on any computing device equipped with a front facing camera, such as a laptop computer, a tablet computing device (e.g., a smart tablet), a smartphone, computerized health related equipment, or the like.

Notably, the present disclosure provides systems and methods that relate to the integration of stimuli design and automatic analysis to assess characteristics, such as midline head postural control, as reflected in the rate of spontaneous head movements during states of active attention as triggered by displayed stimuli. The systems and methods provided herein will allow for more precise, objective, and quantitative characterization of motor signatures thereby providing new automated methods for assessing neurodevelopmental or neuropsychiatric disorders (e.g., such as autism, early autism, early autism spectrum disorders, autism spectrum disorders, etc.) for risk identification and treatment monitoring.

As used herein, the term "brain disorder" refers to any neurological disorder and/or neuropsychiatric disorder of the nervous system involving structural, biochemical, or electrical abnormalities in the brain, spinal cord, or other nerves that may result in a variety of symptoms. In some embodiments, the neurodevelopmental or neuropsychiatric disorder is associated with certain differences in motor function or ability, such as postural control that is reflected in the ability of a subject to maintain a steady head and body position without excessive sway. In some embodiments, the neurodevelopmental or neuropsychiatric disorder is the result of an injury or disease. In other embodiments, the neurodevelopmental or neuropsychiatric disorder comprises a neurological developmental disorder. Examples include, but are not limited to, autism, autism spectrum disorder (ASD), schizophrenia, and attention deficithyperactivity disorder (ADHD), cognitive disorders (also known as neurocognitive disorders), such as Alzheimer's disease, Parkinson's disease, frontotemporal degeneration, Lewy body disease, traumatic brain injury (TBI), prion disease, and dementia/neurocognitive issues due to HIV and other viral infections.

As used herein, "treatment," "therapy" and/or "therapy regimen" refer to the clinical intervention made in response to a disease, disorder or physiological condition (e.g., a neurodevelopmental or neuropsychiatric disorder) manifested by a patient/subject or to which a patient/subject may be susceptible. The aim of treatment includes the diagnosis, alleviation or prevention of symptoms, slowing or stopping the progression or worsening of a disease, disorder, or condition (e.g., a neurodevelopmental or neuropsychiatric disorder) and/or the remission of the disease, disorder or condition (e.g., a neurodevelopmental or neuropsychiatric disorder).

In some embodiments, the disclosed subject matter provides a method of assessing the posture of a subject, the method comprising: (1) recording the face of a subject (e.g., a patient or user) using a front facing camera while the subject views (in the computing platform device's screen) a movie displaying dynamic stimuli with multiple components designed to elicit a positive affect and engage the subject's attention; (2) analyzing facial landmarks on the subject's face; (3) estimating the (i) head pose angle and (ii) number of head pose angles, of the subject based on the analyzed facial landmarks; and (4) compiling the results of steps (2) ands (3), wherein a subject who exhibits more head position movement as compared to a control is assessed as having a neurodevelopmental or neuropsychiatric disorder; and (5) administering to the subject having been diagnosed with a neurodevelopmental or neuropsychiatric disorder an effective therapy or therapies for treating said neurodevelopmental or neuropsychiatric disorder.

In accordance with some aspects of the present subject matter, the postural control assessment and/or analysis may be performed by one or more computing platforms. For example, a tablet computer (e.g., a smart tablet) containing a camera may be usable to execute a postural control assessment engine that can provide stimuli, such as via a short duration video, and can record subject responses to the stimuli via the camera. In this example, the PCAE may be configured to process and/or analyze recorded head movements, e.g., by identifying facial landmarks and estimating a corresponding head pose based on the displacement of the facial landmarks. Continuing with this example, a postural control assessment may be determined using the recorded information to determine whether the degree or magnitude of head movement is indicative of one or more neurodevelopmental or neuropsychiatric disorders.

By providing the disclosed techniques, mechanisms, and/or methods for conducting postural control assessments, diagnosis and/or treatment for various neurodevelopmental or neuropsychiatric disorders (e.g., autism, an anxiety disorder, an aggressiveness disorder, attention deficient and hyperactivity disorder (ADHD), or the like) may be performed promptly and efficiently. Moreover, by providing automated postural control assessments using software executing on mobile devices (e.g., tablet computers) or other relatively inexpensive devices, cost barriers associated with diagnosis and/or treatment of neurodevelopmental or neuropsychiatric disorders may be alleviated. Further, using aspects of the present subject matter, diagnosis and/or treatment for many brain or neurological disorders in young children may be facilitated and/or improved over conventional methods, thereby allowing treatments, strategies, and/or intervention methods to be implemented more broadly and earlier than previously possible with conventional methods. Moreover, using aspects of the present subject matter, consistency of assessment may be improved over conventional methods, e.g., by utilizing automated techniques and precise measurements.

Reference will now be made in detail to exemplary embodiments of the subject matter described herein, examples of which are illustrated in the accompanying drawings. Wherever possible, the same reference numbers will be used throughout the figures and refer to the same or like entities.

FIG. 1 is a diagram illustrating an exemplary computing platform 100 configured for conducting automated postural control assessment according to an embodiment of the subject matter described herein. Computing platform 100 may be any suitable entity, such as a mobile device, a smartphone, a tablet computer, a laptop computer, a personal computer, or the like, that is configurable for performing automated postural control assessments via monitoring and recording subjects for responses to one or more stimuli (e.g., as shown in a video) and automatically analyzing the facial responses and/or head displacement for determining a postural control assessment. In some embodiments, computing platform 100 may include a memory and processor configured for executing a postural control assessment engine (PCAE) 104 (e.g., an app or other software construct) for conducting an automated postural control assessment. Notably, PCAE 104 may be stored in memory (e.g., memory 106) and subsequently executed by the processor(s) 102 of computing platform 100. Processor(s) 102 may represent any suitable device or component (e.g., hardware-based processor) for processing information and executing instructions or operations. Processor 102 may be any type of processor, such as a central processor unit (CPU), a microprocessor, a multi-core processor, and the like. Computing platform 100 may further include a memory 106 for storing information and instructions to be executed by processor 102. In some embodiments, memory 106 can comprise one or more of random access memory (RAM), read only memory (ROM), static storage such as a magnetic or optical disk, or any other type of machine or non-transitory computer-readable medium. Computing platform 100 may further include a communication device (not shown), such as a network interface card (NIC) or other communications interface, configured to provide communications access to various entities (e.g., other computing platforms). In some embodiments, memory 106 may be utilized to store PCAE 104 (for execution by processor 102 as shown in FIG. 1) or software therein, and a PCAE related storage 108.

In this example, computing platform 100 may also include a user interface 110 (e.g., a screen display) for providing/presenting stimuli (e.g., video display and/or audio) designed to prompt certain responses from a subject (e.g., a child or toddler) and a camera for recording or capturing facial responses and head movements to the provided stimuli. Continuing with this example, PCAE 104 may obtain and use the captured head movement displacement responses for determining postural control assessment data and/or a diagnosis of a neurodevelopmental or neuropsychiatric disorder or a related metric, such as a number value between 0 and 10 indicating the likelihood of a subject having a particular neurodevelopmental or neuropsychiatric disorder).

In some embodiments, PCAE 104 may be any suitable entity (e.g., software executing on one or more processors) for performing one or more aspects associated with conducing an automated postural control assessment. For example, PCAE 104 may include or host an application that performs an automated postural control assessment by displaying video stimuli to a subject and determining, based on the facial response and head movement, information utilized for the postural control assessment. In some embodiments, PCAE 104 may be configured to initially instruct user interface 110 to provide at least one display stimulus for prompting a response from a subject viewer, to capture or obtain, using a camera (e.g., camera 112) that is included in and/or communicatively coupled to computing platform 100. User interface 110 may be any interface for providing information (e.g., output) to a subject and/or for receiving information (e.g., input) from the subject. In some embodiments, user interface 110 may include a display screen for displaying various video or movie-based stimuli to prompt a response from a subject. Notably, the response from the subject may include a facial response and/or head movement. PCAE 104 is further configured to determine, using the at least one response, a postural control assessment (and/or postural control assessment data) associated with the subject. In some embodiments, camera 112 comprises a front facing camera may be found in a mobile device or a tablet computer. Camera 112 may represent any suitable entity (e.g., a camera or camera chip in a smartphone or tablet computing device) for recording facial and/or head movements of the subject input (e.g., motion). For example, camera 112 may include a two dimensional camera, a three dimensional camera, a heat-sensor camera, a video camera, or any combination thereof. In some embodiments, camera 112 may be usable for recording a subject during a postural control assessment. In some embodiments, camera 112 may be any stand-alone imaging device whose images are able to be downloaded to a computer or mobile device either wirelessly, via a wired connection (e.g., USB cable), or transferred via a storage device (e.g., SD card, microSD card, etc.). In some embodiments, computing platform 100 and/or PCAE 104 may be communicatively coupled to a user interface 110 and a camera 112.

Memory 106 may be any suitable entity or entities (e.g., non-transitory computer readable media) for storing various information. Memory 106 may include an PCAE related storage 108. PCAE related storage 108 may be any suitable entity (e.g., a database embodied or stored in computer readable media) storing user data, stimuli (e.g., videos or video segments), recorded responses, and/or predetermined information. For example, PCAE related storage 108 may include user data, such as age, name, knowledge, skills, sex, and/or medical history. PCAE related storage 108 may also include predetermined information, including information gathered by clinical studies, patient and/or caregiver surveys, and/or doctor assessments. The predetermined information may include information for analyzing responses, information for determining based responses, information for determining assessment thresholds, coping strategies, recommendations (e.g., for a caregiver or a child), treatment and/or related therapies, information for generating or select videos, video segments or related stimuli for various screen regions usable for an automated attention assessment, and/or other information.

In some embodiments, PCAE related storage 108 or another entity may maintain associations between relevant health information and a given user or a given population (e.g., users with similar characteristics and/or within a similar geographical location). For example, users associated with different conditions and/or age groups may be associated with different recommendations, base responses, and/or assessment thresholds for indicating whether user responses are indicative of neurodevelopmental/psychiatric disorders.

In some embodiments, PCAE related storage 108 may be accessible by PCAE 104 and/or other modules of computing platform 100 and may be located externally to or integrated with PCAE 104 and/or computing platform 100. For example, PCAE related storage 108 may be stored at a server located remotely from a mobile device containing PCAE 104 but still accessible by PCAE 104. In another example, PCAE related storage 108 may be distributed or separated across multiple nodes.

It will be appreciated that the above described modules are for illustrative purposes and that features or portions of features described herein may be performed by different and/or additional modules, components, or nodes. For example, aspects of automated postural control assessment described herein may be performed by PCAE 104, computing platform 100, and/or other modules or nodes.

In some embodiments, PCAE 104 and/or another module may generate, determine, and/or utilize stimuli (e.g., video and/or audio) for eliciting specific facial or head movement responses from a subject. For example, PCAE 104 is configured to display a series of stimuli, comprised of brief movies via a smart tablet device to a subject (e.g., a child sitting on a caregiver's lap). The tablet device may be placed on a stand approximately 3 feet away from the subject to prevent the subject from touching the display screen. The stimuli can comprise a series of brief developmentally-appropriate movies designed to elicit positive affect and engage the subject's attention. As shown in FIG. 3 (and discussed in detail below), the displayed movies include cascading bubbles, a mechanical bunny, animal puppets interacting with each other, and a split screen showing on one side a woman singing nursery rhymes and dynamic noise-making toys on the other side. The time duration lengths of said movies may be 30 seconds (Bubbles), 60 seconds (Rhyme), and ~70 seconds (Bunny and Puppets). In some embodiments, each movie is shown once except for Bubbles which is shown at the beginning and end of the series. The entire series of movies lasts approximately 5 minutes. Examples of the stimuli and experimental setup are presented in FIGS. 2 and 3 (which are described in detail below).

In some instances during the display of three of the movies, the examiner (who is standing behind the subject) called the subject's name loudly. A failure to orient to a called name is an early symptom of autism. However, all segments when a subject looked away from the movie (including when the subject oriented/responded to called name and for all 5 second segments post the name-calling stimulus) were automatically removed from the present analysis. Specifically, in order to remove any influence on head movement or displacement due to the subject orienting when his/her name was called, the time window starting at cue for the name call prompt (e.g., a subtle icon used to prompt the examiner to call the name) through the point where 75% of the audible name calls actually occurred, plus 150 frames (5 seconds) was removed. Notably, since previous studies have shown that orienting tends to occur within a few seconds after a name call, this eliminated segments influenced by the name call.

In some embodiments, a frontal camera in a tablet computing device (e.g., camera 112 of computing platform device 100) is configured to record video of the subject's face at 1280x720 spatial resolution and 30 frames per second. A fully automatic computer vision analysis (CVA) algorithm, which can be incorporated in or as PCAE 104, may detect and track a plurality (e.g., 49) of facial landmarks on the subject's face (see FIG. 2 and accompanying description below). This CVA algorithm and/or PCAE 104 can further estimate head pose angles relative to the camera by computing the optimal rotation parameters between the detected landmarks and a 3D canonical face model. For each video frame, PCAE 104 may output 2D positional coordinates of the facial landmarks and 3 head pose angles: yaw (left-right), pitch (up-down), and roll (tilting left-right). The yaw head pose angle can be used by PCAE 104 to determine the frames when the subject is engaged with the movie stimuli. For example, frames exhibiting a yaw pose with a magnitude less than 20° were considered indicative of the subject being engaged).

In order to quantify a subject's head displacement or movement when the subject is engaged by the video stimuli (e.g., less than 20° yaw), per-frame pixel-wise displacements of a plurality of central facial landmarks can computed and normalized by PCAE 104 with respect to the subject's eye width. As such, the subject's head displacement or movement may be measured by PCAE 104 as a normalized proportion of the subject's eye width per frame. The pixel-wise displacements of the central facial landmarks (e.g., facial landmarks 202-206) are dependent on the subject's distance to the camera in the tablet device (e.g., camera 112 in platform 100). Although the tablet device may be placed approximately 3 feet away from the subject, the subject is free to move throughout the assessment, thus affecting the magnitude of facial landmark displacements. For example, when the subject is near to the camera, the pixel displacements are larger than if the subject performed the same movement but farther away from the camera. However, normalizing the displacements with respect to the eye-width by the PCAE 104 diminishes this distance to camera dependency. Thus, the head movement between frame n and n-1 is defined as the average Euclidean displacements of the central nose, left inner eye, and right inner eye landmarks (see facial landmarks 202-206 in FIG. 2) normalized by a ±1 second windowed-average, centered around frame n, of the Euclidean distances between the inner left and right eye landmarks, $$\frac{\overline{d_{n-1,n}}}{\overline{w_{n-15,n+15}}},$$

where $\overline{d_{n-1,n}}$ is the average landmark displacement of the three central landmarks between frame n and n-1, and $\overline{w_{n-15,n+15}}$ is the average Euclidean distance between the left and right eye landmarks when the subject is engaged between a half-second (15 frames) before and after frame n. As mentioned above, this normalization process can be conducted by PCAE 104.

Figure 2:
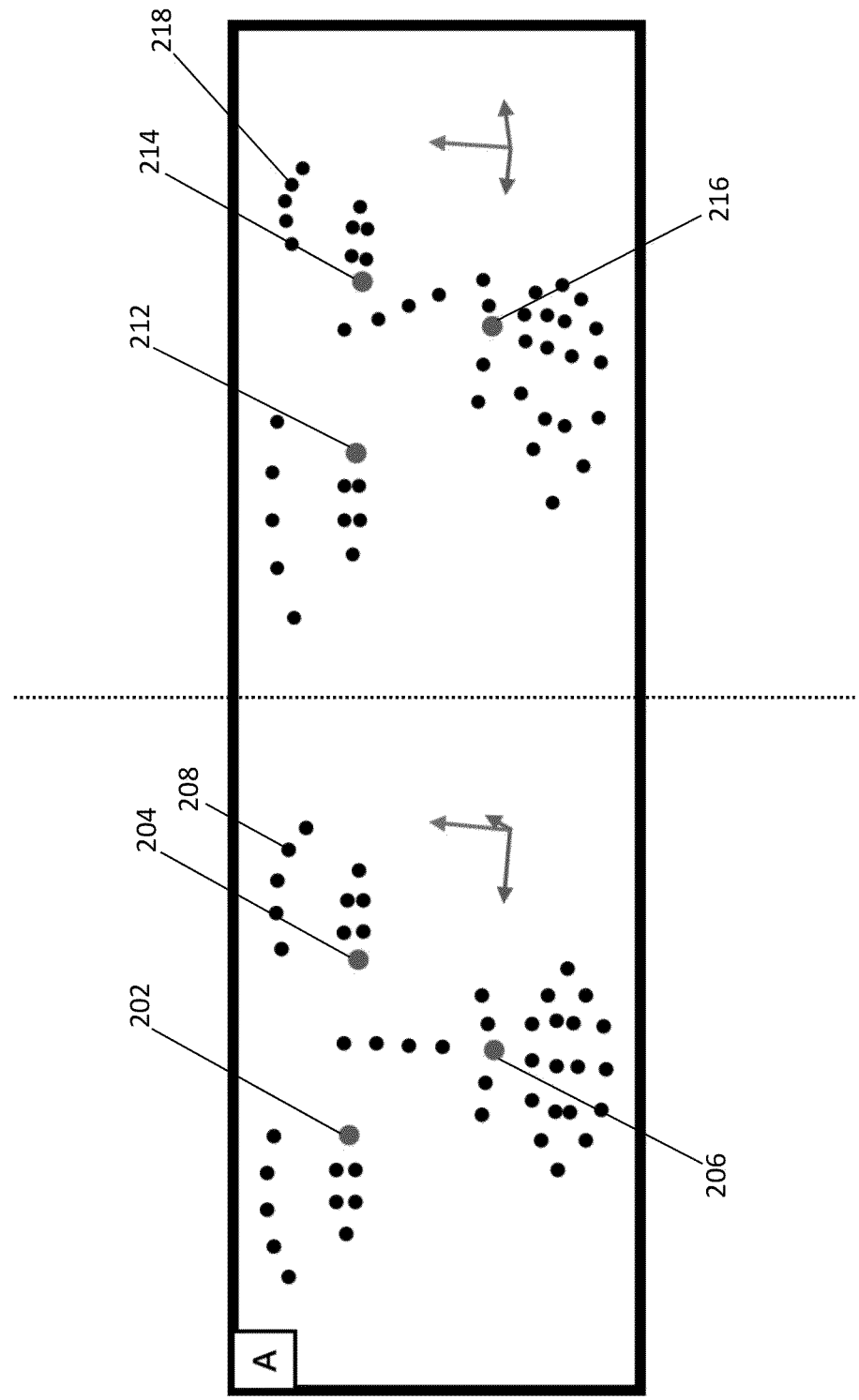
FIG. 2 is a diagram illustrating the detection of facial landmarks for head pose estimation according to an embodiment of the subject matter described herein.
Figure 3:
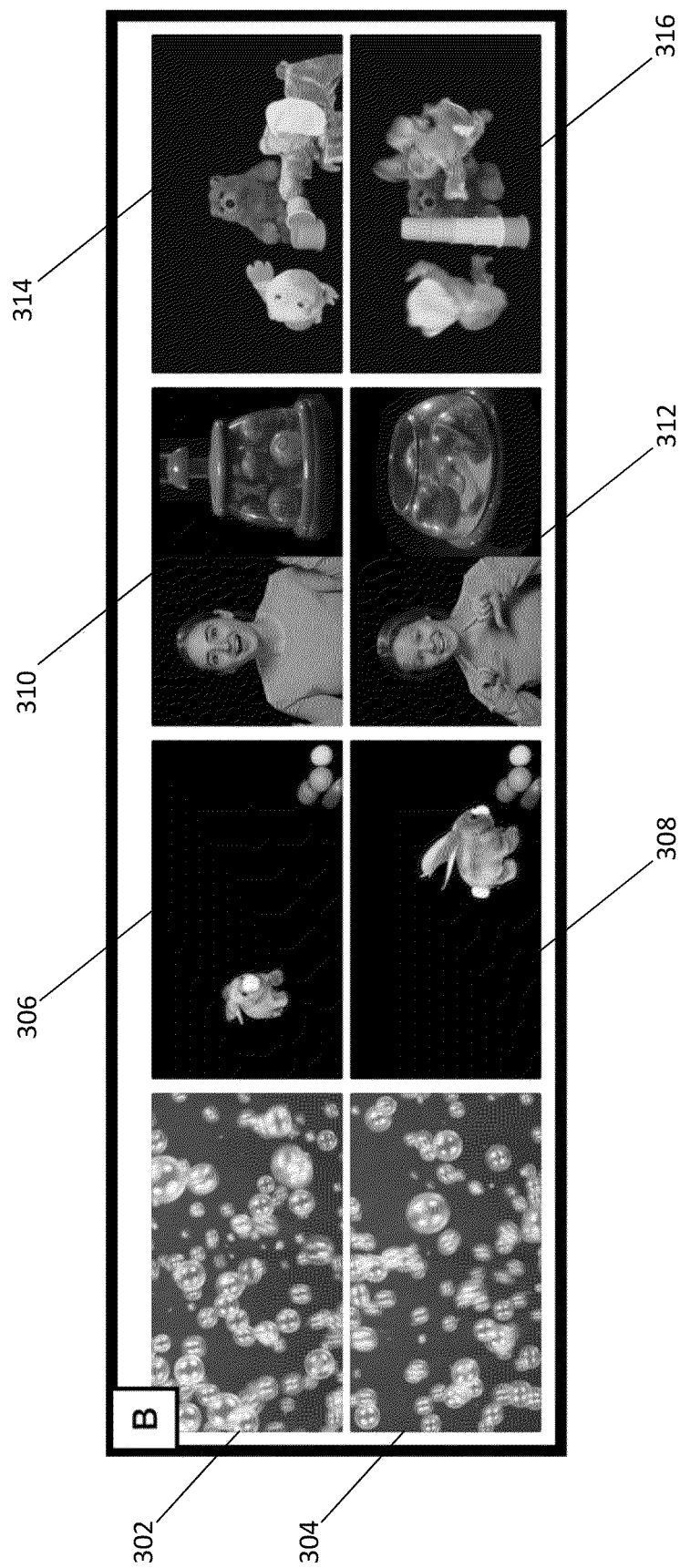
FIG. 3 depicts exemplary images of video frames from movie stimuli displayed by the computing platform according to an embodiment of the subject matter described herein.

FIG. 2 illustrates an exemplary tablet computer movie task and facial landmark detection technique. For example, FIG. 2 depicts two examples of facial landmark points detected by computer vision analysis as executed by the engine. Notably, the black dots shown in FIG. 2 represent designated facial landmark points (e.g., landmark point 208) that may be mapped from a subject's face. In some embodiments, particular facial landmark points may be designated for use by the engine to determine head displacement data. Notably, the engine can utilize facial landmark points 202-206 to compute head movement. As shown in FIG. 2, facial landmark point 202 corresponds with the inner right eye of the subject, facial landmark point 204 corresponds to the inner left eye of the subject, and facial landmark point 206 corresponds to the nose of the subject. In the first example of FIG. 2 (e.g., on the left side), the illustration depicts the facial landmarks and the head pose of a subject that is looking toward and engaged in the video stimuli (i.e., viewing a movie displayed on computing platform device 100). Conversely, the second example of FIG. 2 illustrates the facial landmarks and the head pose of the subject that is gazing in a direction away from the video stimuli (e.g., looking away from the movie displayed on computing platform device 100). For example, facial landmark point 212 corresponds with the inner right eye while subject looks away, facial landmark point 214 corresponds to the inner left eye while subject looks away, and facial landmark point 216 corresponds to the nose while subject looks away). Notably, both states of head displacement are automatically detected by PCAE 104. Additional techniques for identifying and/or detecting facial landmarks is described in U.S. Pat. Application Serial No. 15/141,391, which is herein incorporated by reference in its entirety.

FIG. 3 illustrates exemplary movie stimuli that can be displayed on computing platform device 100. For example, video frames 302 and 304 display different frames of a movie stimuli show comprising bubbles (e.g., a 30 second movie with two repetitions). Similarly, video frames 306 and 308 portray two different time frames corresponding to a bunny movie (e.g., 66 seconds in duration). Likewise, video frames 310 and 312 portrayed two different time frames corresponding to a movie of rhymes (e.g., 60 seconds). Lastly, video frames 314 and 316 portrayed two different time frames corresponding to a puppet show movie (e.g., 68 seconds in duration).

In some embodiments, the original dataset includes frame-by-frame measurements of head movement, with observations for each $1/30^{th}$ of a second. In order to prepare the data for statistical analysis, the movement measurements may be aggregated by PCAE 114, which can be configured to calculate the head movement rate. Notably, the head movement rate can be defined as the moving sum of the cumulative frame-by-frame movement measurements for each 10-frame period (representing $1/3^{rd}$ of a second). If any individual frames within a 10-frame set were set to missing, such as when the facial landmarks were not visible or during the name-call period, the moving sum was also set to missing. Outliers were addressed by Winsorizing to the $95^{th}$ percentile prior to aggregation.

All statistical analyses were performed separately for each of the movie stimuli (e.g., movies shown in FIG. 3). To visualize the time series, PCAE 104 calculated and plotted the median head movement rate as well as the $1^{st}$ and $3^{rd}$ quartiles at each $1/3$ second time interval for both ASD and non-ASD children subjects. Unadjusted and adjusted rate ratios for the association between ASD diagnosis and the rate of head movement in each $1/3$ second time interval may be estimated by PCAE 104 using a generalized linear mixed log-gamma regression model. Adjusted estimates may be controlled by PCAE 104 for race (e.g., white; other races), age (in months), and sex (male; female). To account for potential within-subject correlations due to repeated measurement, a random intercept for each participant can be included by PCAE 104.

Figure 4:
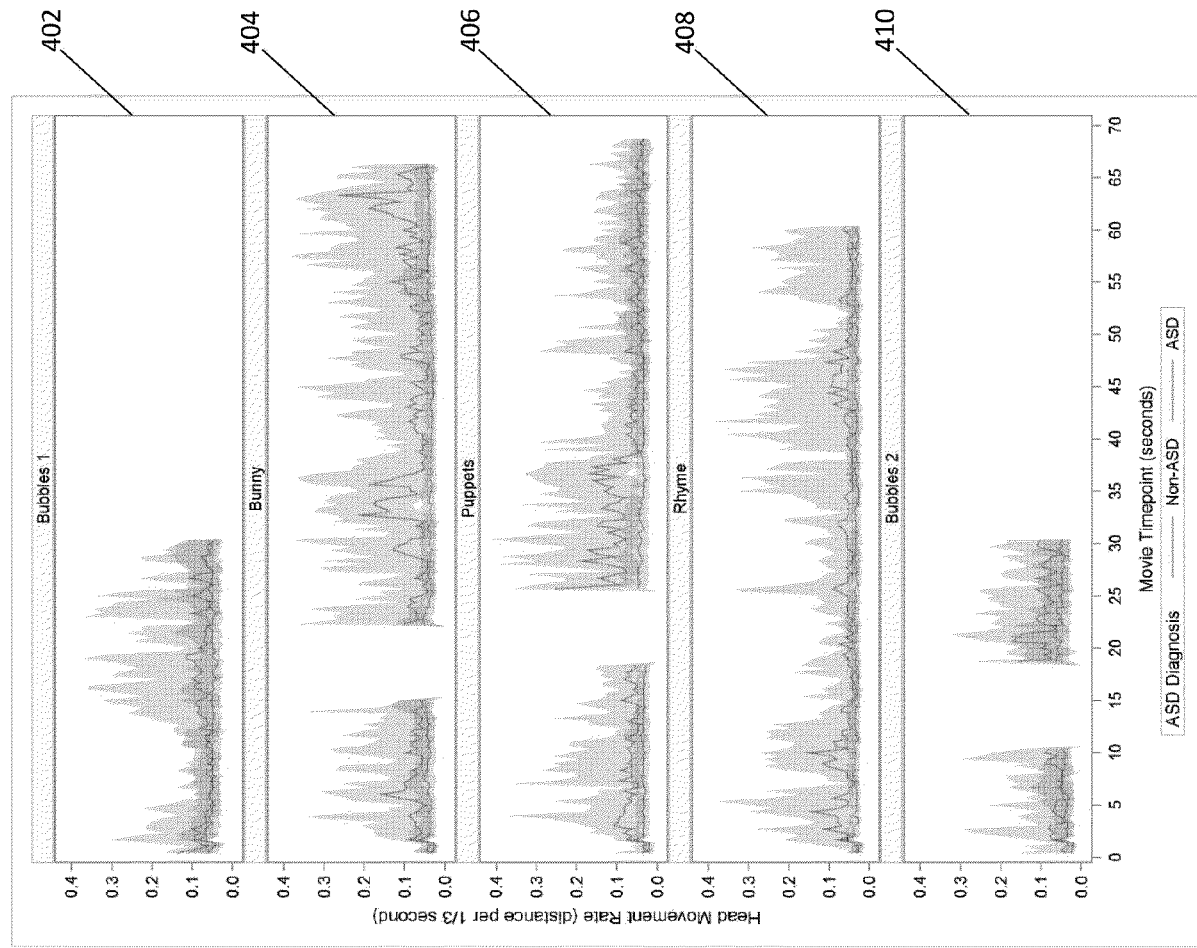
FIG. 4 is a diagram illustrating a time series of head movement rates associated with various movie stimuli according to an embodiment of the subject matter described herein.

FIG. 4 illustrates a plurality of graphs that depict exemplary time series of head movement rates for each of the movie stimuli described above and depicted in FIG. 3. Notably, FIG. 4 includes a time series graph 402 for a first Bubbles movie, a time series graph 404 for the Bunny movie, a time series graph 406 for the Puppets movie, a time series graph 408 for the Rhymes movie, and a time series graph 410 for a second Bubbles ('Bubbles 2') movie. As depicted in each of graphs 402-410, the head movement rate is measures as the distance traveled per $1/3$ second (10 video frames) for each of an ASD diagnosis group and a non-ASD group. Solid lines represent the median values at each time point and bands represent the first and third quartiles at each time point. The blank sections in graphs 402-410 represent name calls. Based on a generalized linear mixed regression model with a log link and gamma distribution (e.g., adjusting for ethnicity/race, age, and sex), significant associations between a diagnostic group (ASD versus non-ASD) and the rate of head movement were found during all movies except for the Bubbles 2 (i.e., the last movie). For Bubbles 2, the shorter duration may have affected power to detect a result as there was nevertheless a trend toward a group difference in the same direction as all other movies. Results of the analysis are shown in Table 1 below:

TABLE 1

Unadjusted and adjusted rate ratios for the associations between diagnostic group and rate of head movement

| Movie | Unadjusted | | Adjusted | |
|---|---|---|---|---|
| | Rate Ratio (95% Confidence Interval) for ASD vs non-ASD | P-value | Rate Ratio (95% Confidence Interval) for ASD vs non-ASD | P-value |
| Video Bubbles 1 | 1.46 (1.09, 1.97) | 0.011 | 1.53 (1.10, 2.12) | 0.012 |
| Video Bunny | 2.13 (1.60, 2.85) | <0.0001 | 2.22 (1.60, 3.07) | <0.0001 |
| Video Puppets | 2.08 (1.50, 2.88) | <0.0001 | 2.30 (1.60, 3.31) | <0.0001 |
| Video Rhymes and Toys | 2.37 (1.77, 3.16) | <0.0001 | 2.45 (1.78, 3.39) | <0.0001 |
| Video Bubbles 2 | 1.52 (1.08, 2.14) | 0.018 | 1.43 (0.97, 2.10) | 0.070 |

Analyzing the results, robust group differences in the rate of head movement were evident during 4 out of 5 of the movies. For example, the rate of head movement among participants with ASD was 2.22 times that of non-ASD participants during the Bunny movie, after adjusting for age, race, and sex (95% Confidence Interval 1.60, 3.07). Further, the rate ratio was higher for all movies that had animated and more complex stimuli (e.g., Bunny, Puppets, Rhymes and Toys), as compared to the less complex Bubbles videos.

Although the language delay (LD)/developmental delay (DD) group was too small to conduct independent analyses of that group, as a sensitivity analysis, the 8 patients with LD/DD were from the main regression model and re-estimated the associations, as shown in Table 2 below.

TABLE 2

Adjusted rate ratios for the associations between diagnostic group and rate of head movement after removing LD/DD participants

| Movie | Adjusted Rate Ratio (95% Confidence Interval) for ASD vs TD | P-value |
|---|---|---|
| Video Bubbles 1 | 1.58 (1.11, 2.24) | 0.0109 |
| Video Bunny | 2.34 (1.67, 3.30) | <0.0001 |
| Video Puppets | 2.38 (1.62, 3.50) | <0.0001 |
| Video Rhymes and Toys | 2.54 (1.81, 3.57) | <0.0001 |
| Video Bubbles 2 | 1.50 (1.00, 2.26) | 0.0496 |

Overall, the results are consistent with those reported in the main analysis. Namely, the associations are slightly stronger when the LD/DD group is removed from the non-ASD group (thereby leaving typical development (TD) subjects). As such, the data produced by utilizing the disclosed subject matter indicates that differences in early motor development are an important feature of ASD. Significant differences in postural control have been found as reflected in differences in the rate of spontaneous movement of the head between (toddler) subjects with ASD versus those subjects without ASD. Using the automated, objective approach afforded by the PCAE 114 of the disclosed subject matter, data comprised of video-frame-level measurements of head movements with observation for each 1/30$^{th}$ of a second and created 10-frame moving sums to capture movement can be detected, monitored, and analyzed. Notably, timeseries data revealed group differences in the rate of head movement across all movies representing a wide range of stimuli, such as bubbles, a hopping bunny, and a woman singing a nursery rhyme paired with dynamic toys. An increase in the rate of head movement observed in young children subjects with ASD during states of engaged attention may indicate underlying differences in the ability to maintain midline postural control and/or atypical engagement of attentional systems in young toddlers with ASD. Notably, these movements were not defined by spontaneous looking away from the stimulus. Rather, the movements were characterized by the subject's failure to keep the head in a still midline position while viewing the movie. This is distinct from studied features that are characterized by greater yaw angular displacement and greater yaw and roll angular velocity, which were primarily present during the presentation of social stimuli and might reflect sensory modulation.

Figure 5:
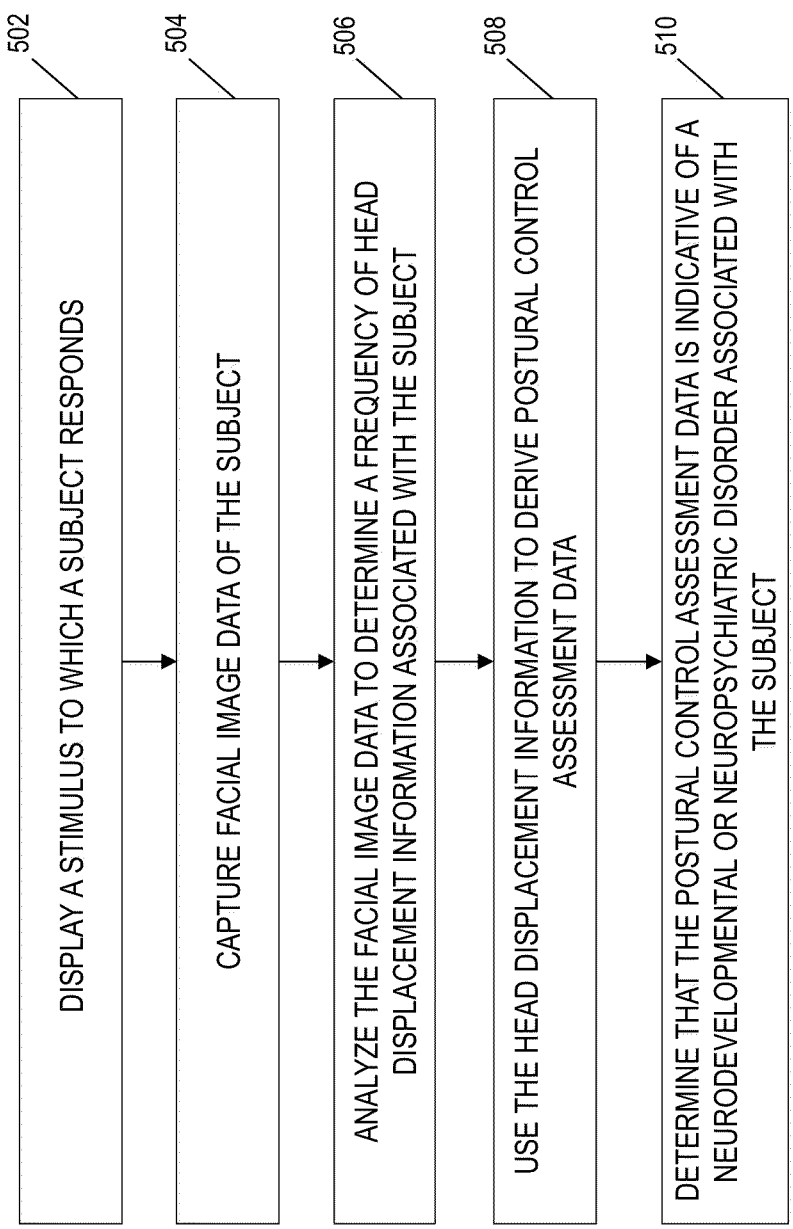
FIG. 5 is flow chart depicting an exemplary process conducting an automatic assessment of postural control of a subject according to an embodiment of the subject matter described herein.

FIG. 5 is a diagram illustrating a process 500 for automated postural control assessment according to an embodiment of the subject matter described herein. In some embodiments, process 500 described herein, or portions thereof, may be performed at or by computing platform 100, PCAE 104, and/or another module or node. For example, computing platform 100 may be a mobile device, tablet computer, or the like and PCAE 104 may include or provide an application running or executing on computing platform 100. In some embodiments, process 500 may include steps 502-510.

In step 502, a stimulus to which the subject responds is displayed. In some embodiments, the computing platform may be configured to present a movie or video to a subject via a screen display or user interface.

In step 504, facial image data of a subject is captured. In some embodiments, a front facing camera of a computing platform device is configured to record and/or capture the facial image data of a subject viewer. For example, the PCAE may trigger the camera to record a subject's responses while a video or movie is presented to the subject via a screen display (e.g., user interface 110). Notably, the computing platform device may be configured to display or provide at least one stimulus for engaging the subject's attention and eliciting a positive affect or response from the subject. Examples of stimuli include video and/or audio media that is presented to the subject.

In step 506, the facial image data is analyzed to determine a frequency of head displacement information associated with the subject. In some embodiments, the PCAE is configured to determine the position of facial landmarks on the subject's face and estimate i) a head pose angle of the subject and ii) a number of head pose angles of the subject based on the analyzed facial landmarks of the subject.

In step 508, the head displacement information is used to derive postural control assessment data. In some embodiments, PCAE is configured to compile the results from the head pose angles of the subject (in step 506) to derive postural control assessment data.

In step 510, the postural control assessment data is determined to be indicative of a neurodevelopmental or neuropsychiatric disorder associated with the subject. In some embodiments, the PCAE may determine that the subject is demonstrating more head position movement or displacement (i.e., postural control assessment data) as compared to a control subject or predefined threshold.

For example, the PCAE may be configure to compare the determined head displacement information and/or postural control assessment data corresponding to the subject to at least one baseline, threshold, or control data set of head displacement data and/or postural control assessment data. In some embodiments, PCAE 104 can be configured to compare the determined head pose angle of the subject (as related to the determined facial landmarks) to a threshold head pose angle values. Notably the threshold head pose angle values can be mapped to one or more neurological or neurological disorders and if met or exceeded, are indicative of said to one or more neurological or neurological disorders. As such, the PCAE can establish that the head displacement is indicative of the subject having a neurodevelopmental or neuropsychiatric disorder. In some embodiments, the subject having been diagnosed with a neurodevelopmental or neuropsychiatric disorder can be administered an effective therapy for treating the diagnosed neurodevelopmental or neuropsychiatric disorder.

In some embodiments, a postural control assessment or related data may be provided to a subject, a medical records system, a service provider, a healthcare provider, a caregiver of the subject, or any combination thereof. For example, where information is provided to a clinician or a medical professional, a postural control assessment may include stimuli used in a test, recording of the subject during the test, test results, and/or other technical or clinical information. In another example, where information is provided to a parent, a postural control assessment may include a metric associated with an easy to understand scale (e.g., 0-100%) for indicating the likelihood of a subject (e.g., a child) having a particular neurodevelopmental or neuropsychiatric disorder and useful suggestions for improving one or more related symptoms associated with the neurodevelopmental or neuropsychiatric disorder.

It will be appreciated that exemplary process 500 is for illustrative purposes only and that different and/or additional actions may be used. It will also be appreciated that various actions associated with exemplary process 500 may occur in a different order or sequence.

It should be noted that computing platform 100, PCAE 104, and/or functionality described herein may constitute a special purpose computing device. Further, computing platform 100, PCAE 104, and/or functionality described herein can improve the technological field of diagnosing and treating various neurodevelopmental or neuropsychiatric disorders by providing mechanisms for automated behavior assessments. Moreover, such mechanisms can alleviate many barriers, including costs, equipment, and human expertise, associated with conventional (e.g., clinical) methods of diagnosis and treatment of neurodevelopmental or neuropsychiatric disorders, e.g., in young children ranging from about 1 to 5 years of age.

Moreover, the present disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Recitation of ranges of values herein are merely intended to serve as a shorthand method of referring individually to each separate value falling within the range, unless otherwise-Indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

The disclosure of each of the following references is incorporated herein by reference in its entirety to the extent not inconsistent herewith and to the extent that it supplements, explains, provides a background for, or teaches methods, techniques, and/or systems employed herein.

REFERENCES

1. Teitelbaum P, Teitelbaum O, Nye J, Fryman J, Maurer RG. Movement analysis in infancy may be useful for early diagnosis of autism. *Proc Natl Acad Sci U S A.* 1998;95(23):13982-13987.
2. Esposito G, Venuti P, Maestro S, Muratori F. An exploration of symmetry in early autism spectrum disorders: analysis of lying. *Brain & development.* 2009;31(2):131-138.
3. Flanagan JE, Landa R, Bhat A, Bauman M. Head lag in infants at risk for autism: a preliminary study. *The American journal of occupational therapy: official publication of the American Occupational Therapy Association.* 2012;66(5):577-585.
4. Zappella M, Einspieler C, Bartl-Pokorny KD, et al. What do home videos tell us about early motor and socio-communicative behaviours in children with autistic features during the second year of life--An exploratory study. *Early human development.* 2015;91(10):569-575.
5. Dawson G, Osterling J, Meltzoff AN, Kuhl P. Case Study of the Development of an Infant with Autism from Birth to Two Years of Age. *Journal of applied developmental psychology.* 2000;21(3):299-313.
6. Brisson J, Warreyn P, Serres J, Foussier S, Adrien-Louis J. Motor anticipation failure in infants with autism: a retrospective analysis of feeding situations. *Autism : the international journal of research and practice.* 2012;16(4):420-429.
7. Gima H, Kihara H, Watanabe H, et al. Early motor signs of autism spectrum disorder in spontaneous position and movement of the head. *Experimental brain research.* 2018;236(4):1139-1148.
8. Hytonen M, Pyykko I, Aalto H, Starck J. Postural control and age. *Acta otolaryngologica.* 1993; 113(2): 119-122.
9. Ghanouni P, Memari AH, Gharibzadeh S, Eghlidi J, Moshayedi P. Effect of Social Stimuli on Postural Responses in Individuals with Autism Spectrum Disorder. *J Autism Dev Disord.* 2017;47(5):1305-1313.
10. Minshew NJ, Sung K, Jones BL, Furman JM. Underdevelopment of the postural control system in autism. *Neurology.* 2004;63(11):2056-2061.
11. Gouleme N, Scheid I, Peyre H, et al. Postural Control and Emotion in Children with Autism Spectrum Disorders. *Translational neuroscience.* 2017;8:158-166.
12. Campbell K, Carpenter KL, Hashemi J, et al. Computer vision analysis captures atypical attention in toddlers with autism. *Autism.* 2018:1362361318766247.
13. Anzulewicz A, Sobota K, Delafield-Butt JT. Toward the Autism Motor Signature: Gesture patterns during smart tablet gameplay identify children with autism. *Scientific reports.* 2016;6:31107.
14. Martin KB, Hammal Z, Ren G, et al. Objective measurement of head movement differences in children with and without autism spectrum disorder. *Molecular autism.* 2018;9:14.
15. Wu D, Jose JV, Nurnberger JI, Torres EB. A Biomarker Characterizing Neurodevelopment with applications in Autism. *Scientific reports.* 2018;8(1):614.
16. Gotham K, Risi S, Pickles A, Lord C. The Autism Diagnostic Observation Schedule: revised algorithms for improved diagnostic validity. *J Autism Dev Disord.* 2007;37(4):613-627.
17. Hashemi J, Campbell K, Carpenter K, et al. A scalable app for measuring autism risk behaviors in young children: A technical validity and feasibility study. Paper presented at: Proceedings of the EAI International Conference on Wireless Mobile Communication and Healthcare; October 14-16 2015; London, Great Britain.
18. De La Torre F. IntraFace. Proceedings of the *IEEE International Conference on Automatic Face and Gesture Recognition Workshops.* 2015.
19. Dementhon DD, L.D.. Model-based object pose in 25 lines of code. *International Journal of Computer Vision.* 1995; 15(1): 123-141.
20. Hashemi J, Tepper M, Vallin Spina T, et al. Computer vision tools for low-cost and noninvasive measurement of autism-related behaviors in infants. *Autism Res Treat.* 2014;2014:935686.
21. Hashemi J, Dawson, G., Carpenter, K.L.H., Campbell, K., Qui, Q., Espinosa, S., Marsa, S., Baker, J.P, Egger, H.L., Sapiro, G.. Computer vision analysis for quantification of autism risk behaviors. *IEEE Transactions on Affective Computing.* 2018:1-1.
22. Heiser P, Frey J, Smidt J, et al. Objective measurement of hyperactivity, impulsivity, and inattention in children with hyperkinetic disorders before and after treatment with methylphenidate. *European child & adolescent psychiatry.* 2004; 13(2):100-104.
23. Reiersen AM, Constantino JN, Todd RD. Co-occurrence of motor problems and autistic symptoms in attention-deficit/hyperactivity disorder. *J Am Acad Child Adolesc Psychiatry.* 2008;47(6):662-672.

24. Cook JL, Blakemore SJ, Press C. Atypical basic movement kinematics in autism spectrum conditions. *Brain : a journal of neurology*. 2013;136(Pt 9):2816-2824.
25. Lim YH, Lee HC, Falkmer T, et al. Effect of Visual Information on Postural Control in Adults with Autism Spectrum Disorder. *J Autism Dev Disord*. 2018.
26. Morris SL, Foster CJ, Parsons R, Falkmer M, Falkmer T, Rosalie SM. Differences in the use of vision and proprioception for postural control in autism spectrum disorder. *Neuroscience*. 2015;307:273-280.
27. Marko MK, Crocetti D, Hulst T, Donchin O, Shadmehr R, Mostofsky SH. Behavioural and neural basis of anomalous motor learning in children with autism. *Brain*. 2015;138(Pt 3):784-797.
28. Esposito G, Venuti P, Apicella F, Muratori F. Analysis of unsupported gait in toddlers with autism. *Brain & development*. 2011;33(5):367-373.

It will be understood that various details of the subject matter described herein may be changed without departing from the scope of the subject matter described herein. Furthermore, the foregoing description is for the purpose of illustration only, and not for the purpose of limitation, as the subject matter described herein is defined by the claims as set forth hereinafter.

What is claimed is:

1. A method for conducting an automatic assessment of postural control of a subject, the method comprising:
    at a computing platform including a processor and memory:
        displaying a stimulus to which a subject responds;
        capturing facial image data of the subject;
        analyzing the facial image data to determine a frequency of head displacement information associated with the subject, wherein analyzing the facial image data to determine the frequency of head displacement information includes measuring head displacement of the subject during a series of frames where the subject is exhibiting a head yaw pose with a magnitude less than a predetermined value;
        using the frequency of head displacement information to derive postural control assessment data; and
        determining that the postural control assessment data is indicative of a neurodevelopmental or neuropsychiatric disorder associated with the subject.

2. The method of claim 1 comprising utilizing facial landmarks on the face of the subject.

3. The method of claim 2 wherein the facial landmarks comprise points corresponding to a nose and edges of eyes of the subject.

4. The method of claim 2 wherein the facial landmarks are normalized in a manner such that the facial landmarks are independent of head displacement or a distance to a display screen of the computing platform.

5. The method of claim 1 comprising administering to the subject an effective therapy for treating the neurodevelopmental or neuropsychiatric disorder.

6. The method of claim 1 wherein the stimulus comprises a video containing dynamic stimuli with multiple components designed for identifying the neurodevelopmental or neuropsychiatric disorder of the subject.

7. The method of claim 1 wherein the neurodevelopmental or neuropsychiatric disorder comprises autism, autism spectrum disorder, or an attention deficit hyperactivity disorder (ADHD).

8. A system for conducting an automatic assessment of postural control of a subject, the system comprising:
    a computing platform including at least one processor and memory, wherein the computing platform is configured to:
        display a stimulus to which a subject responds;
        capture facial image data of the subject;
        analyze the facial image data to determine a frequency of head displacement information associated with the subject, wherein analyzing the facial image data to determine the frequency of head displacement information includes measuring head displacement of the subject during a series of frames where the subject is exhibiting a head yaw pose with a magnitude less than a predetermined value;
        use the frequency of head displacement information to derive postural control assessment data; and
        determine that the postural control assessment data is indicative of a neurodevelopmental or neuropsychiatric disorder associated with the subject.

9. The system of claim 8 wherein the computing platform is further configured to utilize facial landmarks on the face of the subject.

10. The system of claim 9 wherein the facial landmarks comprise points corresponding to a nose and edges of eyes of the subject.

11. The system of claim 9 wherein the facial landmarks are normalized in a manner such that the facial landmarks are independent of head displacement or a distance to a display screen of the computing platform.

12. The system of claim 8 wherein the computing platform is further configured to provide information that is utilized to administer to the subject an effective therapy for treating the neurodevelopmental or neuropsychiatric disorder.

13. The system of claim 8 wherein the stimulus comprises a video containing dynamic stimuli with multiple components designed for identifying the neurodevelopmental or neuropsychiatric disorder of the subject.

14. The system of claim 8 wherein the neurodevelopmental or neuropsychiatric disorder comprises autism, autism spectrum disorder, or an attention deficit hyperactivity disorder (ADHD).

15. A non-transitory computer readable medium comprising computer executable instructions embodied in a computer readable medium that when executed by a processor of a computer control the computer to perform steps comprising:
    at a computing platform including a processor and memory, the computing platform configured for:
        displaying a stimulus to which a subject responds;
        capturing facial image data of the subject;
        analyzing the facial image data to determine a frequency of head displacement information associated with the subject, wherein analyzing the facial image data to determine the frequency of head displacement information includes measuring head displacement of the subject during a series of frames where the subject is exhibiting a head yaw pose with a magnitude less than a predetermined value;
        using the frequency of head displacement information to derive postural control assessment data; and
        determining that the postural control assessment data is indicative of a neurodevelopmental or neuropsychiatric disorder associated with the subject.

16. The non-transitory computer readable medium of claim 15 comprising utilizing facial landmarks on the face of the subject.

17. The non-transitory computer readable medium of claim 16 wherein the facial landmarks comprise points corresponding to a nose and edges of eyes of the subject.

18. The non-transitory computer readable medium of claim 16 wherein the facial landmarks are normalized in a manner that the facial landmarks are independent of head displacement or a distance to a display screen of the computing platform.

19. The non-transitory computer readable medium of claim 15 comprising administering to the subject an effective therapy for treating the neurodevelopmental or neuropsychiatric disorder.

20. The non-transitory computer readable medium of claim 15 wherein the stimulus comprises a video containing dynamic stimuli with multiple components designed for identifying the neurodevelopmental or neuropsychiatric disorder of the subject.

\* \* \* \* \*